US00PP15798P2

(12) United States Plant Patent
Armitage et al.

(10) Patent No.: US PP15,798 P2
(45) Date of Patent: Jun. 14, 2005

(54) GOATSBEARD PLANT NAMED 'MISTY LACE'

(50) Latin Name: ***Aruncus dioicus*×*Aruncus aethusifolius***
Varietal Denomination: Misty Lace

(75) Inventors: Allan M. Armitage, Athens, GA (US); Hazel Y. Wetzstein, Athens, GA (US)

(73) Assignee: The University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 10/738,072
(22) Filed: Dec. 17, 2003
(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—MacCord Mason PLLC

(57) ABSTRACT

A Goatsbeard Plant named 'Misty Lace' is a hybrid between *Aruncus dioicus* and *Aruncus aethusifolius,* and bears distinct habit, having perfect flowers that are borne in feathery, elongate terminal panicles.

1 Drawing Sheet

Botanical description: *Aruncus dioicus*×*Aruncus aethusifolius* Hybrid named 'Misty Lace'.

BACKGROUND OF THE INVENTION

1. Field of the Invention

The present invention comprises a new and distinct plant of *Aruncus,* which has been given the name 'Misty Lace'. The plant is a hybrid between *Aruncus dioicus* and *Aruncus aethusifolius,* and bears distinct habit and floral characteristics which differentiate it from existing cultivars. A number of plants which appeared to be hybrids resulting from open pollination of unnamed species plants growing in the proximity were identified by the inventors in 1999 in Monkton, Md., in the garden of Richard Simon. Three plants were selected by the inventors and taken back to the University of Georgia, Athens, Ga. for subsequent morphological description and evaluation under Southeastern environmental conditions. Of the three evaluated for heat tolerance, only one plant remained alive and thrived and this single plant was identified as the new cultivar. The plant will be used primarily as an ornamental perennial. Asexual reproduction of *Aruncus* 'Misty Lace' has been successfully accomplished through tissue culture protocol, developed by Dr. Wetzstein at the University of Georgia. This is the only means known to the inventors to rapidly reproduce this cultivar for commercial introduction. The instant plant has been consistently produced true to type from tissue culture.

2) Description of Relevant Prior Art

Goatsbeard, the common name for the genus, *Aruncus,* is a well-known genus in ornamental horticulture. Presently, the most common species available commercially is the 1.2–1.8 m common goatsbeard, *A. dioicus,* followed by the dwarf 0.2–0.3 m tall Korean goatsbeard, *A. aethusifolius.* The invention is a hybrid between the two, with a plant height of 0.3–0.5 m. 'Misty Lace' is distinguished from all other varieties of *Aruncus* known to the inventors by its plant and leaf size.

SUMMARY OF THE INVENTION

*Aruncus* 'Misty Lace' is a hybrid between *A. dioicus* and *A. aethusifolius,* with intermediate plant and leaf size.

BRIEF DESCRIPTION OF DRAWINGS

The accompanying illustration shows characteristics of the new cultivar in a photograph as true to color as is reasonably possible to make in illustrations of this nature.

BOTANICAL DESCRIPTION OF THE PLANT

Figure 1:
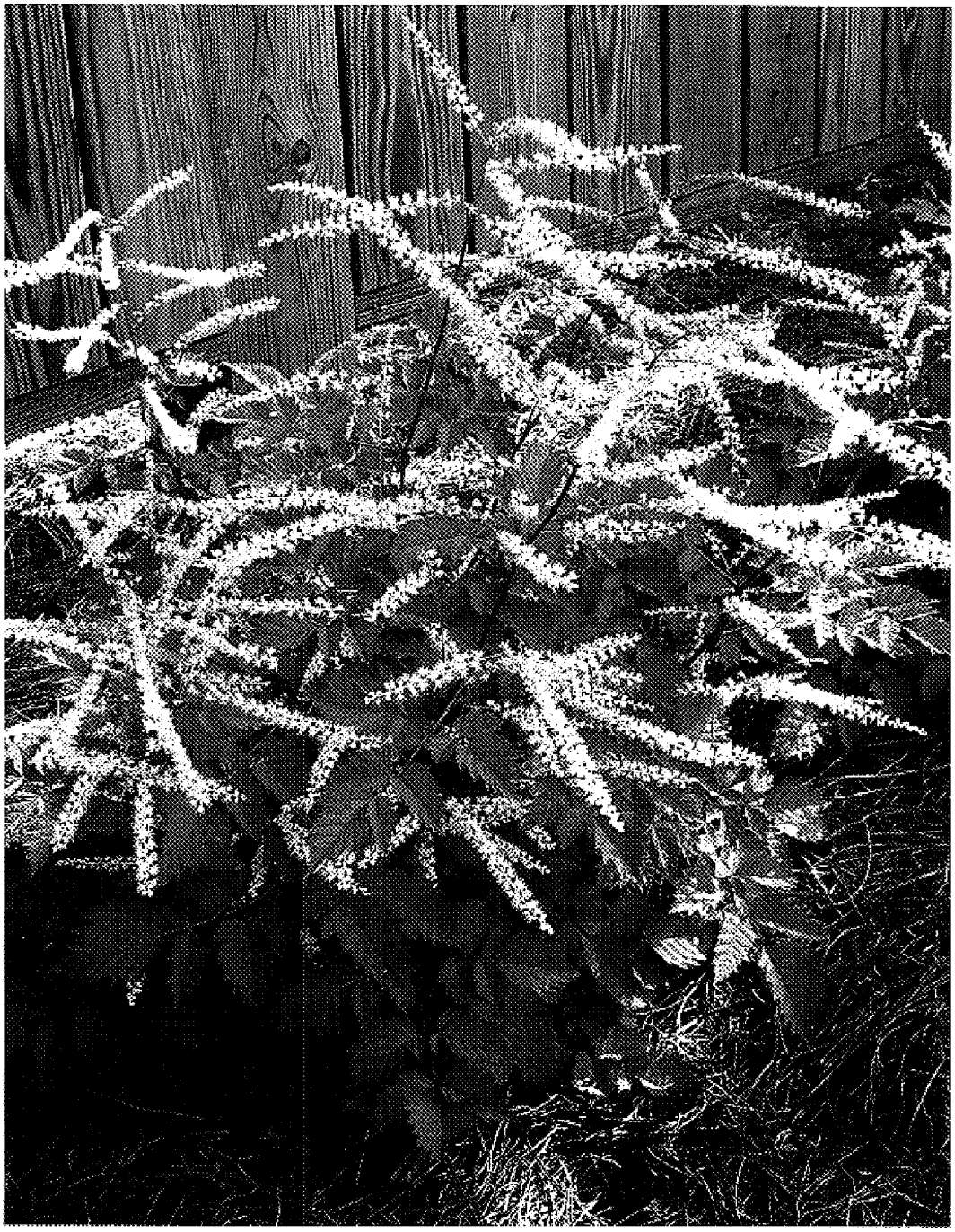
FIG. 1 shows the habit and flowers of a typical 1 year old specimen growing in the University of Georgia Trial Gardens in Athens, Ga.

This plant is a rhizomatous herbaceous perennial species that generally grows 30–50 cm tall at maturity in Georgia. It is a hybrid between the 2 species, *A. aethusifolius* and *A. dioicus* and is distinguished by having an intermediate habit between the two, although it favors *A. aethusifolius* in height. The following description defines the overall appearance of one year old plants as grown under normal conditions in The University of Georgia Horticultural Trial Gardens in Athens, Ga., U.S.A. (USDA Zone 7b). The summers are hot and humid ranging from 75–100 F. (24–38 C.) the average being ~85 F. (29 C.), and winters with average day temperatures of approximately 40 F. (4 C.) Colors are based on The Royal Horticultural Color Chart (1995).

Plant: The plant is conical to pyramidal with an upright habit, and is 30–50 cm high and 30–50 cm in diameter.

Stems: The plants have rounded stems, averaging 25.4 cm in length and 3–5 mm in diameter, above which is the terminal peduncle, the flower stem. The internode length varies from 3.8–5.1 cm and the color is RHS 145A during the early spring, and RHS 137A during the summer months.

Leaf: Leaves occur basally and on the stem and are approximately 12–16 cm long and up to 15 cm wide at their furthest point. Leaflets are doubly serrate in margin with an acuminate apex and rounded base and a glabrous upper and lower surface. The leaflets themselves range from 2–4 cm in length and 2–3 cm in width. The colors of the upper and lower surfaces of the leaves are RHS 137 A and RHS 137C, respectively. Leaves are arranged alternately and are bi- to tri-pinnately compound with one ovate terminal leaflet and 3–4 pairs of pinnately arranged side leaflets. The leaves are petiolate with the petiole being on average 6 cm long with the terminal leaflet and the first side pair being sessile or essentially sessile, with petiole less than 0.5 cm. The remaining 2–3 leaflet pairs are petiolate with the petiole being 0.5 cm on the second side pair and 1–2 cm on the remaining 1–2 side pairs. Table 1 presents a comparison of leaf and plant measurements and flower color among 'Misty Lace' and its parent species, *A. aethusifolius* and *A. dioicus*.

TABLE 1

Average leaf size, plant height and flower color for selected *Aruncus* species

| | Leaf Length (cm) | Leaf Width (cm) | Height of Mature Plant (cm) | Color of Flower RHS |
|---|---|---|---|---|
| *A.* 'Misty Lace' | 14 | 13 | 30–50 | 155A |
| *A. aethusifolius* | 10 | 9 | 20–40 | 155C |
| *A. dioicus* | 90 | 75 | 122–182 | 155D |

Inflorescense: Flowers are perfect and are borne in feathery, elongate terminal and axillary panicles. All flowers in the inflorescence are similar in size and color, with the peduncle averaging 2–4 cm in length and 1 cm diameter. The color of the peduncle is RHS 137A. The mature terminal inflorescences are approximately 18 cm in length and 1.3 cm in diameter, and contain approximately 250 flowers per panicle. The axillary inflorescences are approximately 10 cm in length, 1.3 cm in diameter, and consist of approximately 35 flowers.

The corolla is campanulate in shape with a diameter of 3–4 mm, and contains 5 petals which are spatulate in shape, 1–2 mm in length, and 2–3 mm wide with an obtuse apex, oval base and entire margin. The color of both surfaces is RHS 155 A.

There are 5 sepals, which are 1 mm in length and less than 1 mm in width, ovate in shape with acuminate apex, oval base and entire margin. The color is RHS 143 A.

The flower contains 3 pistils which are 2–3 mm in length and the 3 stigmas are RHS 155 B in color. There are 15 to 20 anthers, 2–3 mm in length and RHS 155 A in color. The pollen has not been characterized.

The buds are oval in shape, 1 to 2 cms in length, and 0.5 cm in diameter, with a color of RHS 145 A and RHS 179 A tips.

*Timing.*—Flowers are produced in mid and late spring, May–June in Athens, Ga. Plants, which were grown in 4 inch (10 cm) containers, were placed in the Horticulture Trial Garden at the University of Georgia in the spring of 2001. After one winter, plants averaged four stems with three inflorescences each. At the end of the second and subsequent winters, plants averaged 8 stems with 4–6 inflorescences each. Individual flowers and inflorescence last from 5 to 10 days depending on the weather conditions. The plant carries inflorescences for up to 5 weeks depending on the weather conditions.

*Fragrance.*—None.

*Seed.*—Seed has been observed, 1 to 3 per ovary, but viability is unknown, although no seedlings have ever been observed by the inventors. The seed is caudate in shape with a reticulated seed coat, about 2 mm in length with a color of RHS 165A.

Other characteristics: The plant has been observed for four years in Athens, Ga. and has thrived in the heat and humidity in the garden. In general, *Aruncus* do poorly under such conditions, but this plant has been perfectly adaptable to at least USDA zone 7b conditions. Also, in 2002–2003, plants were trailed at the University of Georgia Blairsville Research Station, the University of Florida, Gainesville, Fla., the JC Raulston Arboretum, Raleigh, N.C., the Chicago Botanic Garden, the University of Maine, Orono, Me., and the Ulbrich Botanic Garden, Madison Wis. In all cases except Gainesville, Fla., plants survived the winter of 2002 and flowered in the spring of 2003.

Disease/pest resistance: No specific disease or pests of the instant plant have been observed by the inventors under the conditions under which the plant has been grown in Athens.

It is claimed:

1. A new and distinct *Aruncus* plant, as herein shown and described.

* * * * *